(12) United States Patent
Stavnitzky et al.

(10) Patent No.: US 9,551,570 B2
(45) Date of Patent: Jan. 24, 2017

(54) THREE DIMENSIONAL OPTICAL SENSING THROUGH OPTICAL MEDIA

(75) Inventors: Jason Stavnitzky, St George (CA); Ian Cameron, Petersburg (CA)

(73) Assignee: ATS AUTOMATION TOOLING SYSTEMS INC., Cambridge, Ontario (CA)

( * ) Notice: Subject to any disclaimer, the term of this patent is extended or adjusted under 35 U.S.C. 154(b) by 816 days.

(21) Appl. No.: 13/435,768

(22) Filed: Mar. 30, 2012

(65) Prior Publication Data

US 2012/0249749 A1 Oct. 4, 2012

Related U.S. Application Data

(60) Provisional application No. 61/470,393, filed on Mar. 31, 2011.

(51) Int. Cl.
| | |
|---|---|
| *G01B 11/245* | (2006.01) |
| *G01B 21/20* | (2006.01) |
| *G01N 21/41* | (2006.01) |
| *G01N 21/90* | (2006.01) |
| *H04N 13/02* | (2006.01) |

(52) U.S. Cl.
CPC ............. *G01B 11/245* (2013.01); *G01B 21/20* (2013.01); *G01N 21/41* (2013.01); *G01N 21/9018* (2013.01); *H04N 13/0239* (2013.01)

(58) Field of Classification Search
None
See application file for complete search history.

(56) References Cited

U.S. PATENT DOCUMENTS

| | | | | |
|---|---|---|---|---|
| 5,414,474 A | * | 5/1995 | Kamada et al. | 348/700 |
| 5,699,444 A | * | 12/1997 | Palm | 382/106 |
| 6,072,903 A | * | 6/2000 | Maki et al. | 382/190 |
| 6,081,324 A | * | 6/2000 | Yagita et al. | 356/237.1 |
| 6,535,210 B1 | * | 3/2003 | Ellenby et al. | 345/419 |
| 6,621,921 B1 | * | 9/2003 | Matsugu et al. | 382/154 |
| 7,710,391 B2 | | 5/2010 | Bell et al. | |
| 2002/0061130 A1 | * | 5/2002 | Kirk et al. | 382/154 |
| 2002/0103617 A1 | * | 8/2002 | Uchiyama et al. | 702/150 |
| 2005/0219523 A1 | * | 10/2005 | Onuma et al. | 356/239.5 |
| 2006/0012675 A1 | * | 1/2006 | Alpaslan et al. | 348/51 |

(Continued)

FOREIGN PATENT DOCUMENTS

| | | |
|---|---|---|
| DE | 3712958 C1 | 10/1988 |
| GB | 2195178 | 3/1988 |

(Continued)

OTHER PUBLICATIONS

Narita D. et al. "Measurement of 3-D Shape and Refractive Index of a Transparent Object using Laser Rangefinder". Instrumentation and Measurement Technology Conference, Ottawa, Ontario, Canada, May 16-29, 2005, IEEE., vol. 3, Piscataway, NJ, May 16, 2005, pp. 2247-2252.

(Continued)

*Primary Examiner* — Peter D Le
(74) *Attorney, Agent, or Firm* — Gowling WLG (Canada) LLP; Neil Henderson

(57) ABSTRACT

A method of optical sensing comprising generating optical data associated with an object of interest, generating non-optical data associated with the object of interest, and analyzing the optical and non-optical data.

13 Claims, 2 Drawing Sheets

(56) References Cited

U.S. PATENT DOCUMENTS

| | | | |
|---|---|---|---|
| 2006/0152589 A1* | 7/2006 | Morrison | G06K 9/209 348/208.1 |
| 2008/0146932 A1 | 6/2008 | Chalana et al. | |
| 2009/0317002 A1 | 12/2009 | Dein | |
| 2010/0079598 A1 | 4/2010 | Ke et al. | |
| 2012/0038746 A1* | 2/2012 | Schroeder | 348/47 |

FOREIGN PATENT DOCUMENTS

| | | |
|---|---|---|
| JP | 07-083632 | 3/1995 |
| JP | 09-231370 | 9/1997 |
| JP | 2000-193827 | 7/2000 |
| JP | 2004-301825 | 10/2004 |
| JP | 2005-017004 | 1/2005 |
| JP | 2006-106950 | 4/2006 |
| JP | 2006-146766 | 6/2006 |
| JP | 2006-194705 | 7/2006 |
| JP | 2007-163173 | 6/2007 |
| JP | 2007-278989 | 10/2007 |
| WO | 9410532 | 5/1994 |
| WO | 2008130903 | 10/2008 |

OTHER PUBLICATIONS

European Patent Office, Extended European Search Report on EP Appln. No. 12765933.2, dated Sep. 10, 2014.

International Searching Authority (CA), International Search Report and Written Opinion for International Patent App. No. PCT/CA2012/050196, Jun. 27, 2012.

Japan Patent Office, Office Action on Japanese Patent Appln. No. 2014-501378, dated Jan. 5, 2016.

Japan Patent Office, Patent Abstracts of Japan for Japanese Patent Publication No. 2007-163173, Jun. 28, 2007.

Japan Patent Office, Patent Abstracts of Japan for Japanese Patent Publication No. 2000-193827, Jul. 14, 2000.

Japan Patent Office, Patent Abstracts of Japan for Japanese Patent Publication No. 2006-106950, Apr. 20, 2006.

Japan Patent Office, Patent Abstracts of Japan for Japanese Patent Publication No. 2006-146766, Jun. 8, 2006.

Japan Patent Office, Patent Abstracts of Japan for Japanese Patent Publication No. 2006-194705, Jul. 27, 2006.

Japan Patent Office, Patent Abstracts of Japan for Japanese Patent Publication No. 07-083632, Mar. 28, 1995.

Japan Patent Office, Patent Abstracts of Japan for Japanese Patent Publication No. 09-231370, Sep. 5, 1997.

Japan Patent Office, Patent Abstracts of Japan for Japanese Patent Publication No. 2005-017004, Jan. 20, 2005.

Japan Patent Office, Patent Abstracts of Japan for Japanese Patent Publication No. 2007-278989, Oct. 25, 2007.

Japan Patent Office, Patent Abstracts of Japan for Japanese Patent Publication No. 2004-301825, Oct. 28, 2004.

* cited by examiner

THREE DIMENSIONAL OPTICAL SENSING THROUGH OPTICAL MEDIA

CROSS-REFERENCE TO RELATED APPLICATION

This application claims the benefit of U.S. Provisional Patent Application No. 61/470,393 filed Mar. 31, 2011, which is incorporated herein by reference.

FIELD OF THE DISCLOSURE

The present disclosure relates generally to optical, imaging or vision sensing. More particularly, the present disclosure relates to methods and systems for three dimensional optical sensing through differing optical media.

BACKGROUND OF THE DISCLOSURE

Conventional extraction of three-dimensional (3D) structure and/or position of an object may have limitations in that it is typically assumed that the object and any media around it presents simple and well behaved optical properties in the optical sensing of the object. If this limitation of well-behaved optical properties does not hold then conventional techniques will generally not produce precise results of a level that may be required in some applications. Similarly, if the sensing of 3D structure and/or position needs to be repeated for a plurality of similar objects, variation among the objects or variation among the media around the objects may cause further difficulties.

As such, there is a need for improved systems and methods of optical sensing through differing optical media.

SUMMARY OF THE DISCLOSURE

In a first aspect, the present disclosure provides a system and method for using an optical sensor to determine the three dimensional structure or position of an object of interest while taking into account and adjusting for refraction and other optical effects of media that are between the optical sensor and the object of interest.

An intended advantage of systems and methods herein is to provide more detailed data or information about objects that are behind optical media.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Generally, the present disclosure provides methods and systems for sensing objects in three dimensions (3D) through differing optical media. The system includes at least one sensor which captures images of the object and takes into account the medium within which the object is located as well as the medium or mediums between the sensor and the object.

Figure 1:
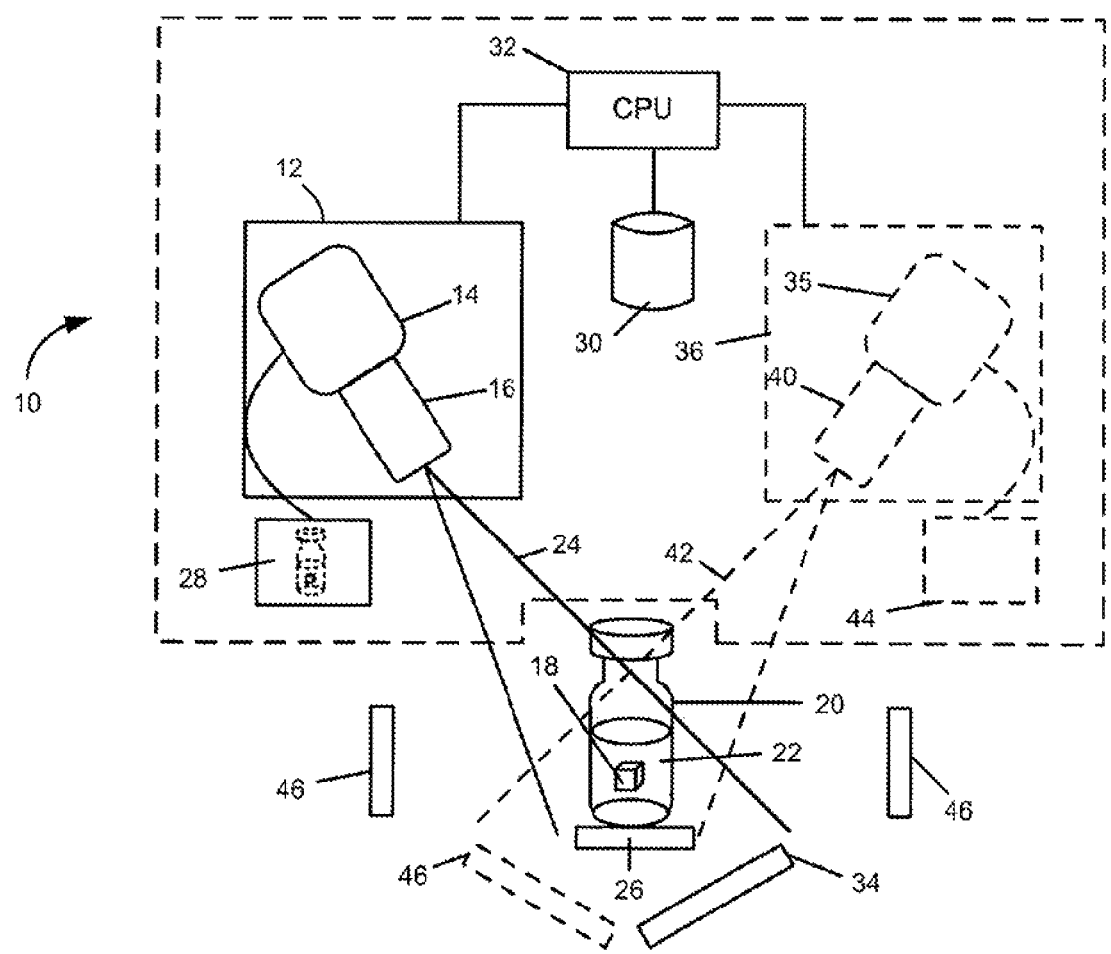
FIG. 1 is a perspective view of a system for imaging an object.

Turning to FIG. 1, a system for sensing (or, in particular, imaging) an object is shown. The system 10 includes an imaging system, such as optical sensor 12 which comprises a camera 14 and a connected lens 16. The primary camera 14 and connected lens 16 are used for producing optical images of items of interest such as, but not limited to, one or more objects 18 within a container 20. In the current embodiment, the container 20, such as a vial or a flask, also includes a fluid 22. In another embodiment, the optical image produced by the optical sensor 12 may be used to assist in determining if particulates are present within the container 20 which may result in the container 20 being deemed contaminated and therefore does not pass a quality assurance test.

FIG. 1 also illustrates an angle of view 24 of the optical sensor 12 with respect to the container 20, which is preferably located atop a platform 26. The resulting image which is captured by the optical sensor 12 is then transmitted to a display 28 or stored in a memory database 30 via a processor 32, or both. The system 10 may also include a background portion 34 which may be provided to assist with determining the position and/or optical properties of the image. In a preferred embodiment, the background portion 34 is either black or white or a combination to assist in reflecting light from the optical sensor 12 back towards the lens to produce the optical image.

As will be described below, the processor 32 also includes software to assist in analyzing the image, or raw image data which is received from the optical sensor 12 or stored in the database 30.

In some embodiments, the system 10 may include a secondary imaging system, or optical sensor 36. The secondary optical sensor 36 preferably includes a camera 38 and connected lens 40. The secondary optical sensor 16 is also used to capture images of the item of interest but from a different direction than the first optical sensor 12. As shown an angle of view 42 for the secondary optical sensor is non-parallel to the angle of view 24 of the first optical sensor 12. In one embodiment, the angles of views 24 and 42 are perpendicular to each other but other angled relationships are contemplated. As with the first optical sensor 12, the resulting image may be displayed on a display 44 or stored in the database 30. To assist in the image capture, the system 10 may include a second background 46.

In operation, the first optical sensor 12 generates the optical image of any item or items of interest, or objects within the container in the angle of view 24. In one embodiment, the optical image may contain two or three dimensional data depending on the type of camera 14 being used. Similarly, if the secondary optical sensor 36 is installed, camera 38 may also produce a two or three dimensional image of the item or items of interest in the container 20.

In order to obtain an improved understanding of the actual positioning of the objects 18 within the container 20, it would be beneficial to review more than just the captured image or images. In current systems, the resulting image that is displayed or stored does not take into account various optical properties, such as for example, the index of refraction, reflectivity or the like, of the media (such as the air between the lens and the container, the walls of the container 20 or the fluid 22). If one is trying to determine the actual position of items of interest within the container, these properties should be taken into account. As understood, the angle of refraction and reflectivity alter the direction of the light from the optical sensor. Without taking these factors into account, the image produced by the optical sensor, either 12 or 36 may give an apparent position of the object 18 that may not be the object's actual or true position within the container 20. For systems where determination of the position of an object 18 within a container 20 is required, having a more accurate representation of the object's true position within the container is more beneficial such as is provided by the current system 10.

In the current system, the optical properties of each of these materials/media and spatial location are analyzed and combined with the image or the raw data to provide an improved understanding of the position of the object 18 within the container 20.

In some embodiments, if the first optical sensor 12 is unable to generate sufficient data to generate full three dimensional data, the secondary optical sensor 36 may be used to assist in generating or obtaining the missing information. Although only two optical sensors are shown, any number of optical sensors may be positioned around the platform for capturing images of the container from different angles of view in order to obtain the required three dimensional data or information.

As shown in FIG. 1, the system 10 may further include a set of reflectors 46 to assist in generating further views of the items of interest however, these are optional and may be included in the system, depending on how the optical sensor or sensors are set up. As understood, the image captured by the secondary optical sensor 36 by itself is also reflective of the apparent position of the object 18 within the container 20 and likely not the true position. The system 10 may also include sensors for capturing non-optical data, as will be discussed below. For instance, information associated with the temperature or position and other physical properties of the media may be sensed and stored in the processor or database 30.

In one embodiment, with a plurality of cameras, the data from the cameras, or optical sensors, and the optical properties and positions of the media such as the air, fluid 22 and walls of the container 20, can then be used to yield an improved three dimensional structure or position of the object 18.

In a single optical sensor embodiment, the system 10 images the items of interest through differing optical media present in the angle of view 24. The differing optical media may include two or more optical media and may include gas, liquid or solid in any order.

In order to assist in the determination of the more accurate representation of the position of the object 18 within the container 20 information or data associated with the container, media, backgrounds, fluid may be stored in the database 30 or in the memory of the processor 32. This may be seen as non-optical data or information. Non-optical data or information may include, but is not limited to, alignment of the lens 16 or 40, distance between the lens 16 or 40 and the surface of the container 20, the thickness of the container wall, the geometry of the container 20, the curvature of the wall of the container 20, the size of the container 20, the volume of the container, the transparency of the container 20, the type of background being used, the pattern of the background being used, the type of fluid 22, the transparency of the fluid 22, the type of medium (fluid, or gas) within the container 20, the size range of the item of interest, the shape range of the item of interest, the level of the fluid within the container or the index of reflection or refraction of the media or medium. Alternatively, the non-optical data, or a priori knowledge, may be provided from an external source.

Figure 2:
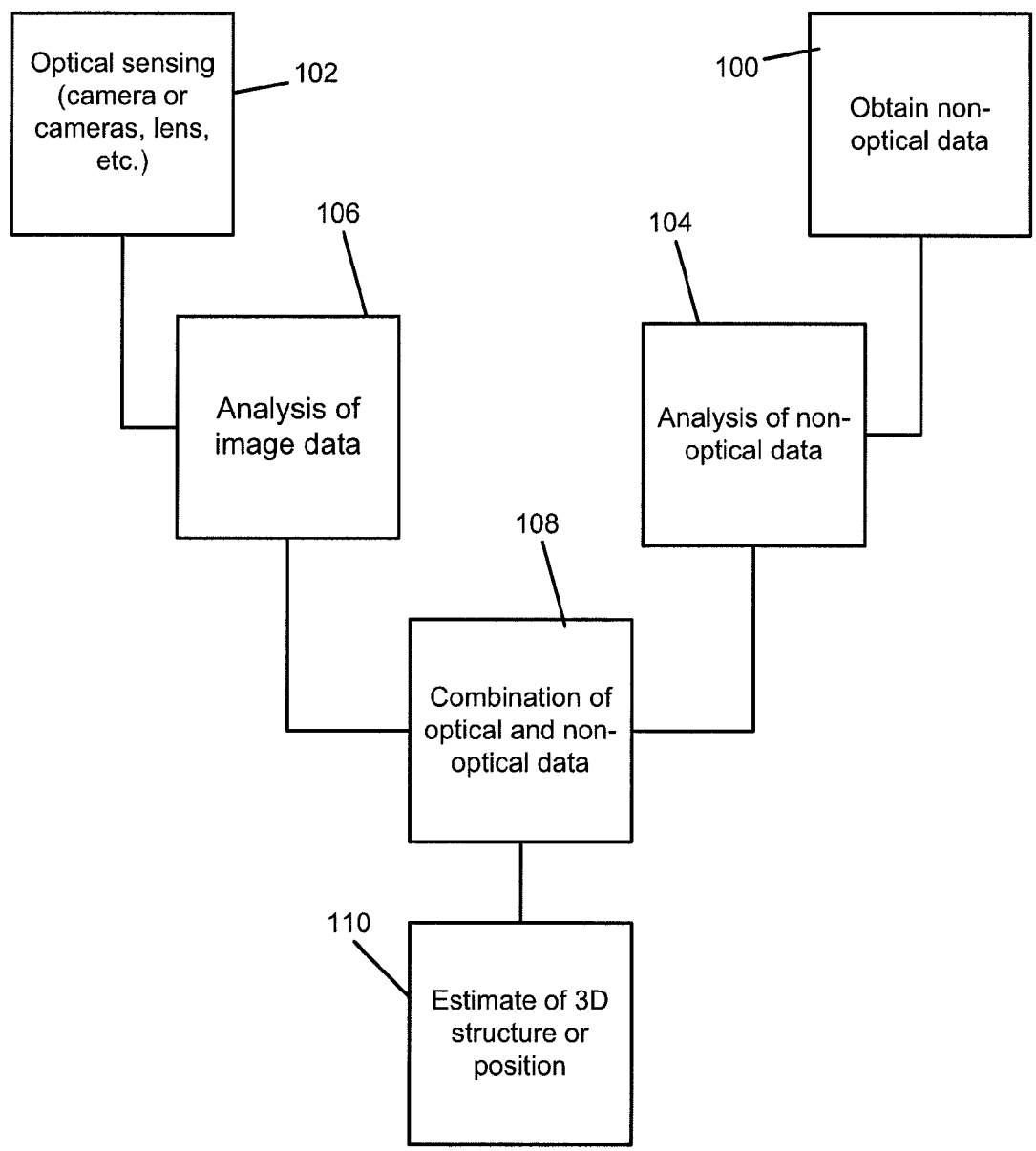
FIG. 2 is a flowchart of the method for determining the 3D measurement.

Referring now to the flowchart shown in FIG. 2, a method of capturing images is shown. In one embodiment, this method may be used to assist in determining the true position of particulates within a vial of medication to determine if the medication is contaminated or may be released to the public. In another embodiment, the image may be used to provide a better understanding of the true position of an item of interest within a container, such as if the item of interest is located on a wall of the container or floating in a fluid within the container.

Initially, there is a determination that one wishes to confirm the true position of an item of interest within a container. The container may then be placed on the platform within the imaging system for image capture.

Any non-optical data, such as those listed above, may be obtained 100 by the processor 32 such as by receiving manual input from the user or tester or based on instructions by the user via a user interface to obtain the relevant non-optical data from the database 30. Before, after or simultaneously with obtaining the non-optical data, an optical image of the container may be obtained 102 by the optical sensor or optical sensors, depending on the set-up of the system 10. The capture of an optical image using a optical sensor will be understood by one skilled in the art. In one embodiment, the optical sensing 102 may be visible or non-visible (for example, infra-red or the like) and may result in two dimensional or three dimensional data.

The non-optical data is then processed and analyzed 104 by the processor 32 while the optical data is also processed and analyzed 106 by the processor 32. In one embodiment, the processing and analysis of the non-optical data is performed to determine the potential contribution of the non-optical information to the image capture. The processing and analysis 106 of the optical data may involve using at least one image analysis technique such as edge-detection, reducing the raw image data, image calibration, or feature point extraction, or other like techniques or by using proprietary analysis techniques. After the optical and non-optical data have been analyzed, the information is combined 108 to produced a set of object positioning data. In an alternative embodiment, the optical data and the non-optical data may be combined before being processed and analyzed to produce the set of object positioning data. For instance, in one example, the index of refraction of the wall of the container may be combined with the optical image data to determine if the item of interest is located on a wall of a container. This may not be readily obvious from a two or three-dimensional image based on just the raw optical data.

The set of object positioning data may then be used to produce a more accurate estimate or representation of the position of the item of interest 110 within the container than can be provided by just the optical image itself.

A particular application for the embodiments described herein is the detection of particulates in a fluid in a glass or plastic carrier. The identification of particulates in a fluid may be important in quality control, particularly in the field of medicines. Embodiments herein are also intended to allow the detection of whether or not an object, such as a particulate, is inside or outside of a container.

In the quality control embodiment, the system 10 may be used in which a plurality of items of interest are sensed and analyzed over time. In this case, the material properties and geometry of each item of interest can differ. Further, the position, geometry and material properties of the optical media can also vary. One aspect herein is that the media do not need to be homogeneous and optical effects can vary throughout (for example, heat haze) as the inclusion of the non-optical data in the creation of the final image takes these factors into account.

In the preceding description, for purposes of explanation, numerous details are set forth in order to provide a thorough understanding of the embodiments. However, it will be apparent to one skilled in the art that these specific details are not required. In other instances, well-known structures are shown in block diagram form in order not to obscure the understanding. For example, specific details are not provided as to whether the embodiments described herein are implemented as a software routine, hardware circuit, firmware, or a combination thereof. It will be understood that many software implementations may also be implemented in hardware.

Embodiments of the disclosure can be represented as a computer program product (software) stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art without departing from the scope of this disclosure.

The invention claimed is:

1. A method of optical sensing of an object of interest in a fluid in a container, the container in a media, the method comprising:
   determining non-optical data relating to the container, the fluid, and a background wherein the background is placed outside the container;
   storing the non-optical data in a memory component;
   determining optical image data associated with the object of interest through the container and the fluid;
   retrieving, from the memory component, the determined non-optical data relating to the container, the fluid, and the background;
   analyzing the optical image data and non-optical data; and
   determining a position of the object of interest with respect to the container and the fluid based on the analyzing of the optical image data and non-optical data.

2. The method of claim 1 further comprising:
   displaying an image of the object of interest based on the analyzed optical image data and non-optical data.

3. The method of claim 1 wherein analyzing optical image data and non-optical data comprises:
   combining the optical image data and non-optical data to produce adjusted image data.

4. The method of claim 1 wherein analyzing optical image data and non-optical data comprises:
   using image analysis techniques to adjust the optical image data based on the non-optical data to provide adjusted image data.

5. The method of claim 4 wherein the image analysis techniques are selected from the group consisting of: edge detection, reducing raw image data, image calibration and feature point extraction.

6. A system for producing an image of an object of interest in a fluid in a container, the container in a media, the system comprising:
   at least one optical sensor for capturing optical image data associated with the object, the optical sensor directed at the object at a predetermined viewing angle, and the optical image data captured through the container and the fluid;
   at least one non-optical sensor for capturing non-optical data relating to the container, the fluid, and a background wherein the background is placed outside the container;
   a memory component for storing the determined non-optical data;
   a processor for receiving the optical image data and retrieving the non-optical data associated with the object and configured to process the optical image data and the non-optical data to form the image and determine a position of the object of interest with respect to the container and the fluid based on the image.

7. The system of claim 6 the at least one optical sensor comprises a first optical sensor and a second optical sensor and the second optical sensor is for capturing second optical image data associated with the object, the second optical sensor directed at a second viewing angle different from the predetermined viewing angle.

8. The system of claim 7 wherein the second viewing angle is perpendicular to the predetermined viewing angle.

9. The system of claim 6 wherein the at least one optical sensor comprises a camera and a lens.

10. The system of claim 6 further comprising a reflector plate, whereby the object is located between the at least one optical sensor and the reflector plate.

11. The system of claim 6 wherein the at least one source for determining non-optical data comprises a set of sensors.

12. The method of claim 1 wherein the non-optical data is selected from a group comprising: temperature; alignment of a lens; distance between the lens and a surface of the container; thickness of a container wall; geometry of the container; curvature of the wall of the container; size of the container; volume of the container; transparency of the container; type of reflector plate; pattern of the reflector plate; type of fluid; transparency of fluid; type of medium within the container; size range of the object of interest; shape range of the object of interest; level of fluid within the container; refraction of the medium; and reflectivity of the medium.

13. The system of claim 6 wherein the non-optical data is selected from a group comprising: temperature; alignment of a lens; distance between the lens and a surface of the container; thickness of a container wall; geometry of the container; curvature of the wall of the container; size of the container; volume of the container; transparency of the container; type of reflector plate; pattern of the reflector plate; type of fluid; transparency of fluid; type of medium within the container; size range of the object of interest;

shape range of the object of interest; level of fluid within the container; refraction of the medium; and reflectivity of the medium.

\* \* \* \* \*